US012678156B2

(12) United States Patent
Smith

(10) Patent No.: US 12,678,156 B2
(45) Date of Patent: Jul. 14, 2026

(54) MEDICAL/VETERINARY SUTURE CRIMP TOOL

(71) Applicant: MWI Veterinary Supply Co., Boise, ID (US)

(72) Inventor: Graham Smith, Newburyport, MA (US)

(73) Assignee: MWI Veterinary Supply Co., Boise, ID (US)

( * ) Notice: Subject to any disclaimer, the term of this patent is extended or adjusted under 35 U.S.C. 154(b) by 217 days.

(21) Appl. No.: 18/456,634

(22) Filed: Aug. 28, 2023

(65) Prior Publication Data

US 2024/0215976 A1     Jul. 4, 2024

Related U.S. Application Data

(60) Provisional application No. 63/477,671, filed on Dec. 29, 2022.

(51) Int. Cl.
*A61B 17/04* (2006.01)

(52) U.S. Cl.
CPC .. *A61B 17/0487* (2013.01); *A61B 2017/0488* (2013.01)

(58) Field of Classification Search
CPC ........ A61B 17/0487; A61B 2017/0488; A61B 2017/0454
See application file for complete search history.

(56) References Cited

U.S. PATENT DOCUMENTS

| | | | |
|---|---|---|---|
| 3,857,396 A | 12/1974 | Hardwick | |
| 4,354,628 A | 10/1982 | Green | |
| 4,637,084 A * | 1/1987 | Wood | H01R 43/0421 |
| | | | 72/409.14 |
| 5,669,917 A * | 9/1997 | Sauer | A61B 17/0487 |
| | | | 606/232 |
| 6,152,188 A | 11/2000 | Barlasov | |
| 6,395,010 B1 | 5/2002 | Wotton, III | |
| 7,121,307 B2 | 10/2006 | Nasiatka et al. | |

(Continued)

OTHER PUBLICATIONS

Written Opinion of the International Searching Authority for International Application No. PCT/US2023/073036 dated Dec. 26, 2023, six (6) pages.

*Primary Examiner* — Jing Rui Ou
(74) *Attorney, Agent, or Firm* — Iandiorio Teska & Coleman, LLP

(57) ABSTRACT

A medical/veterinary suture crimp tool includes a stationary jaw at a distal end of a fixed shank and having across its width and extending at least partially along its length spaced fixed crimp members including at least first, second, and third crimp members and a moveable jaw at a distal end of a linearly driven crossbar and having across its width and extending at least partially along its length, spaced crimp members including at least fourth, fifth, and sixth crimp members opposing, respectively, the first, second, and third crimp members of the stationary jaw. An alignment fiduciary is associated with said fifth crimp member of the stationary jaw for alignment with an alignment fiduciary of a crimp tube. A first handle is connected to the fixed shank and a second handle is pivotably connected to the fixed shank and configured to drive the crossbar linearly with respect to the fixed shank to fully crimp the crimp tube.

8 Claims, 6 Drawing Sheets

(56) References Cited

U.S. PATENT DOCUMENTS

| | | | |
|---|---|---|---|
| 7,691,107 B2 | 4/2010 | Schneiter | |
| 8,495,902 B2 | 7/2013 | Wotton, III | |
| 2002/0120282 A1* | 8/2002 | Kilpela | A61B 17/82 |
| | | | 606/157 |
| 2006/0156784 A1 | 7/2006 | Reedy et al. | |
| 2009/0248063 A1 | 10/2009 | Wotton, III | |
| 2021/0015479 A1 | 1/2021 | Smith | |

* cited by examiner

MEDICAL/VETERINARY SUTURE CRIMP TOOL

RELATED APPLICATIONS

This application claims benefit of and priority to U.S. Provisional Application Ser. No. 63/477,671 filed Dec. 29, 2022, under 35 U.S.C. §§ 119, 120, 363, 365, and 37 C.F.R. § 1.55 and § 1.78, which is incorporated herein by this reference.

FIELD OF THE INVENTION

This subject invention relates to crimping devices typically used in connection with crimp tubes used in medical and veterinary procedures.

BACKGROUND OF THE INVENTION

Crimping devices and crimp tubes are used in procedures such as cruciate ligament stabilization where two ends of a suture (e.g., a mono-filament) are held together in a crimp tube or clamp. A crimping device deforms the crimp tube and locks the suture ends therein. See U.S. Pat. Nos. 6,395,010; 8,495,902; and U.S. Patent Publication No. 2009/0248063 both incorporated herein by this reference.

It is important that the crimping action be precise. Too much pressure on the suture can cause breakage of the suture. If the crimp tube is not deformed enough, on the other hand, the suture can slip in the crimp tube.

The above references disclose crimping devices with spaced opposing crimping members. Each crimping action of these devices results in a single crimp in the crimp tube. Known devices for forming multiple crimps are typically large, complex, and involve multiple jaws. See U.S. Pat. Nos. 7,121,307; 6,152,188; and U.S. 2006/0156784 all incorporated herein by this reference.

It is often necessary to provide more than one crimp in a crimp tube. When using some crimping tools, a first crimp must be made, the tool then relocated to another location on the crimp tube in order to make a second crimp, and so on. Each change of tool location can lend itself to errors.

U.S. Pat. No. 8,495,902, incorporated herein by this reference, discloses a crimping device designed with first and second jaws each including multiple but offset crimping members resulting from a crimp tube with a torturous internal channel providing a strong suture holding strength and requiring only a single crimping action as opposed to multiple crimping actions.

But, the commercial embodiment of the '902 patent, Securos, Inc.'s "Power-X" product, was sometimes hard to use properly by people with less powerful hands and/or for thick walled crimp tubes even though the "Power-X" device featured a double-action handle.

A Ronguer is used to remove hard body tissue and includes a cutting surface linearly driven towards a fixed second cutting surface. See U.S. Pat. No. 7,691,107 incorporated herein by this reference.

BRIEF SUMMARY OF THE INVENTION

The Ronguer handle allows better visibility than plier-type handles but was never to our knowledge used for crimping, especially for imparting multiple crimps at once, because the Ronguer handle was thought to not supply enough force. But, if the wall thickness of the crimp tube is reduced and the crimp tube is partially pre-crimped, then a modified Ronguer handle can be employed to impart multiple crimps at once in the crimp tube with better visibility and still the holding strength of the crimp tube is adequate and in some cases even better because the pre-crimped tube avoids crossing of the sutures within the tube.

Featured is a medical/veterinary suture crimp tool comprising a stationary jaw at a distal end of a fixed shank and having across its width and extending at least partially along its length spaced fixed crimp members including at least first, second, and third crimp members and a moveable jaw at a distal end of a linearly driven crossbar and having across its width and extending at least partially along its length, spaced crimp members including at least fourth, fifth, and sixth crimp members opposing, respectively, the first, second, and third crimp members of the stationary jaw. An alignment fiducial is associated with said fifth crimp member of the stationary jaw for alignment with an alignment fiducial of a crimp tube. A first handle is connected to the fixed shank and a second handle is pivotably connected to the fixed shank and configured to drive the crossbar linearly with respect to the fixed shank to fully crimp the crimp tube.

In one example, the second handle includes a distal socket about a drive member on the crossbar to linearly drive the crossbar. The crimping system may further include a stop limiting the extent of the travel of the crossbar.

Also featured is a crimp tool comprising a stationary jaw at a distal end of a fixed shank and having spaced multiple crimp members each configured to provide a deformation on one side of a crimp tube; a moveable jaw at a distal end of a linearly driven crossbar and having spaced multiple crimp members each configured to provide a deformation on an opposite side of the crimp tube thereby creating multiple crimps in the crimp tube when the stationary and moveable jaws are brought together about the crimp tube, each deformation on one side of the crimp tube opposing the deformation on the opposite side of the crimp tube; an alignment fiducial associated with at least one crimp member for alignment with an alignment fiducial of a crimp tube; a first handle connected to the fixed shank; a second handle pivotably connected to the fixed shank; and means for driving the crossbar linearly with respect to the fixed shank to fully crimp the crimp tube and impart multiple crimps on each side of the crimp tube.

In one example, the means for driving includes a distal socket on the second handle about a drive member on the crossbar to linearly drive the crossbar.

The crimp tube preferably has an oval cross-sectional shape.

In one example, the stationary jaw includes at least partially along its length spaced fixed crimp members including at least first, second, and third crimp members and the moveable jaw includes at least across its width and partially along its length at least fourth, fifth, and sixth crimp members opposing, respectively, the first, second, and third crimp members of the stationary jaw.

Also featured is a method of crimping a suture. Opposite ends of a suture are placed through a crimp tube having an oval cross-sectional shape and a centrally located fiducial. A fiducial of a crimp tool is aligned with the centrally located fiducial of the crimp tube. The crimp tube is crimped by the crimp tool which simultaneously deforms 1) one side of the crimp tube at locations at and on opposite sides of the centrally located fiducial and 2) an opposite side of the crimp tube at locations at and on opposite sides of the centrally located fiducial.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
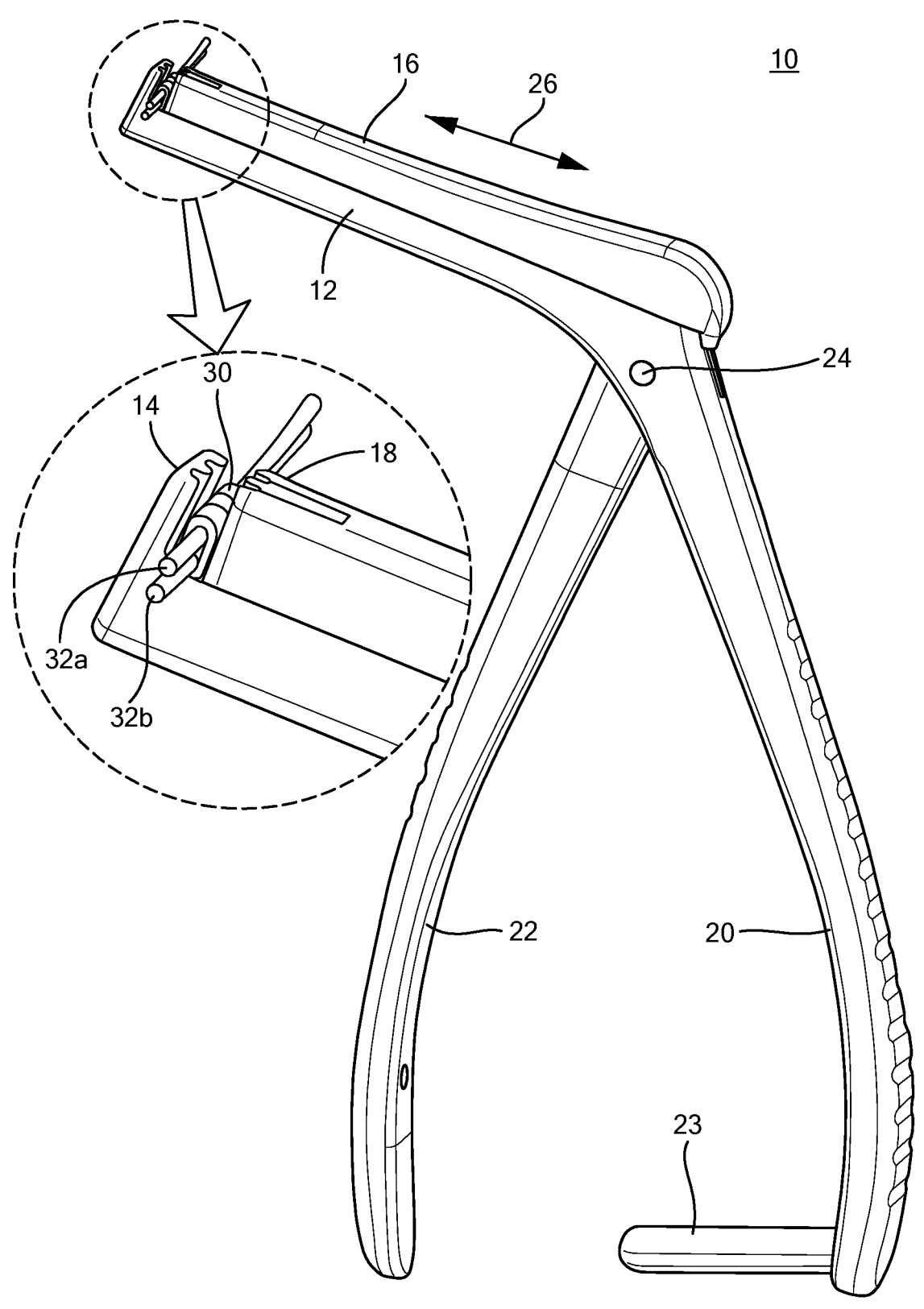
FIG. 1 is a schematic view showing an example of a new medical/veterinary suture crimp tool.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

Shown in FIG. 1 is an example of a medical crimper 10 including fixed shank 12 with stationary jaw 14 at the distal end of shank 12 and linearly driven crossbar 16 with moveable jaw 18 at the distal end of crossbar 16. Handle 20 is connected to fixed shank 12 and handle 22 is pivotally connected to fixed shank 12 at pin 24 and is configured to drive crossbar 16 linearly with respect to fixed shank 12 as shown by arrow 26 to fully crimp crimp tube 30 to secure suture ends 32a and 32b threaded into crimp tube 30. Stop member 23 of handle 20 strikes handle 22 and prevents the jaws from closing any further so as not to over-crimp a crimp tube. This stop member, however, could be associated with jaw 16, for example.

Figure 2:
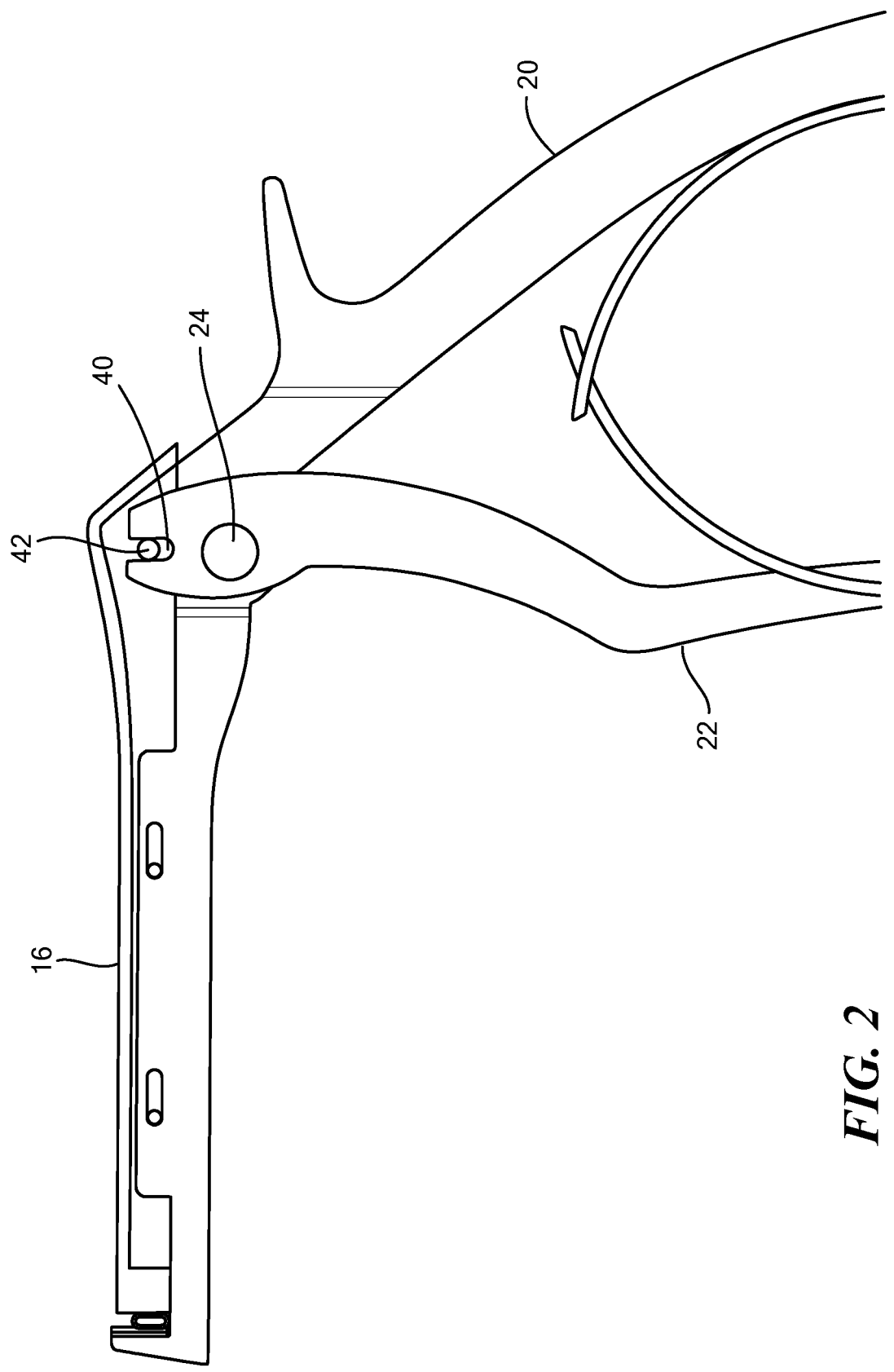
FIG. 2 is a schematic side view of the crimp tool of FIG. 1.

In one example, handle 22, FIG. 2, includes distal socket 40 about drive member 42 extending outward from the side of crossbar 16 to drive the crossbar when handle 22 is closed relative to handle 20. Other means for driving crossbar 16 via handle 22 are possible.

Figure 3:
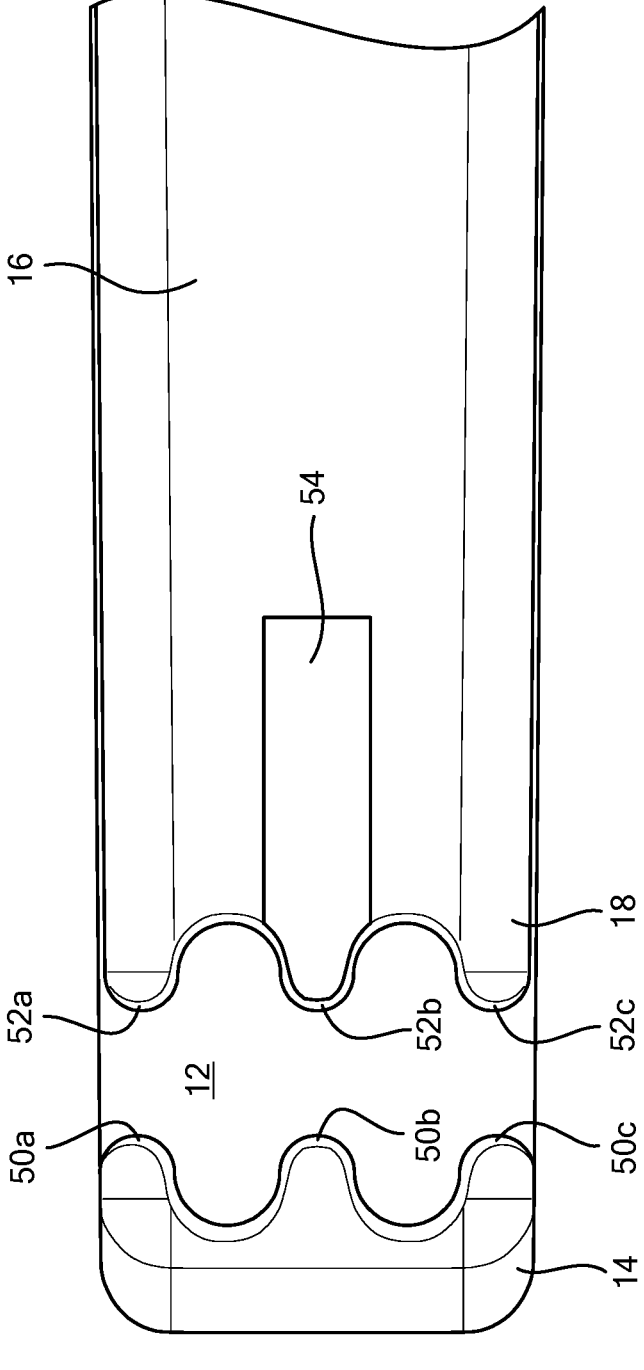
FIG. 3 is a schematic bottom view showing the crimp tool jaws each with a plurality of crimp members.

As shown in FIG. 3 (and FIGS. 5-6), stationary jaw 14 includes, across its width and extending at least partially along its length, spaced fixed crimp members 50a, 50b, and 50c and moveable jaw 18 includes, across its width and at least partially across its length spaced crimp members 52a, 52b, and 52c which oppose, respectively, crimp members 50a, 50b, and 50c of jaw 14.

Figure 4:
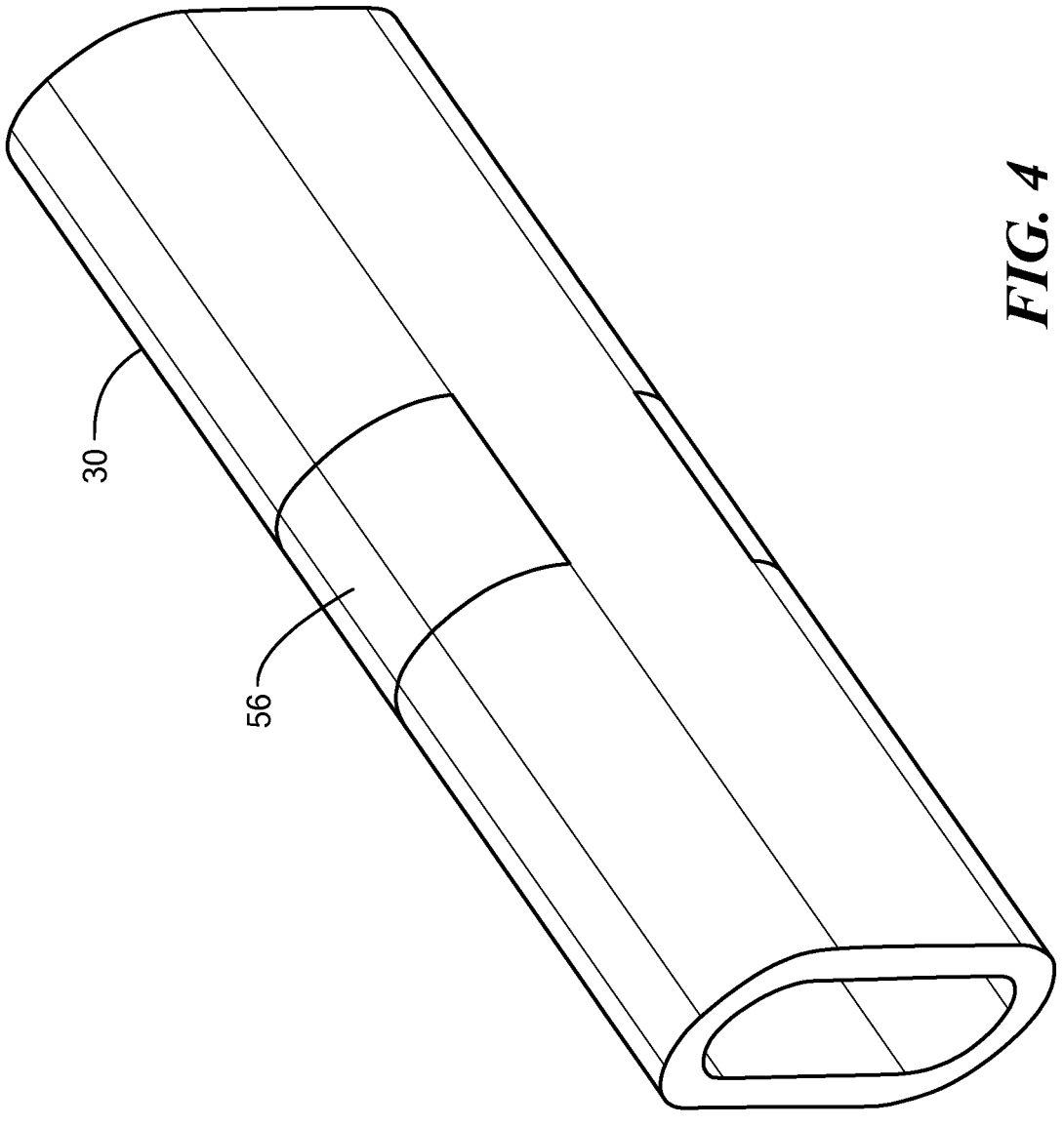
FIG. 4 is a schematic view showing an example of a preferred crimp tube for use with the crimp tool.
Figure 5:
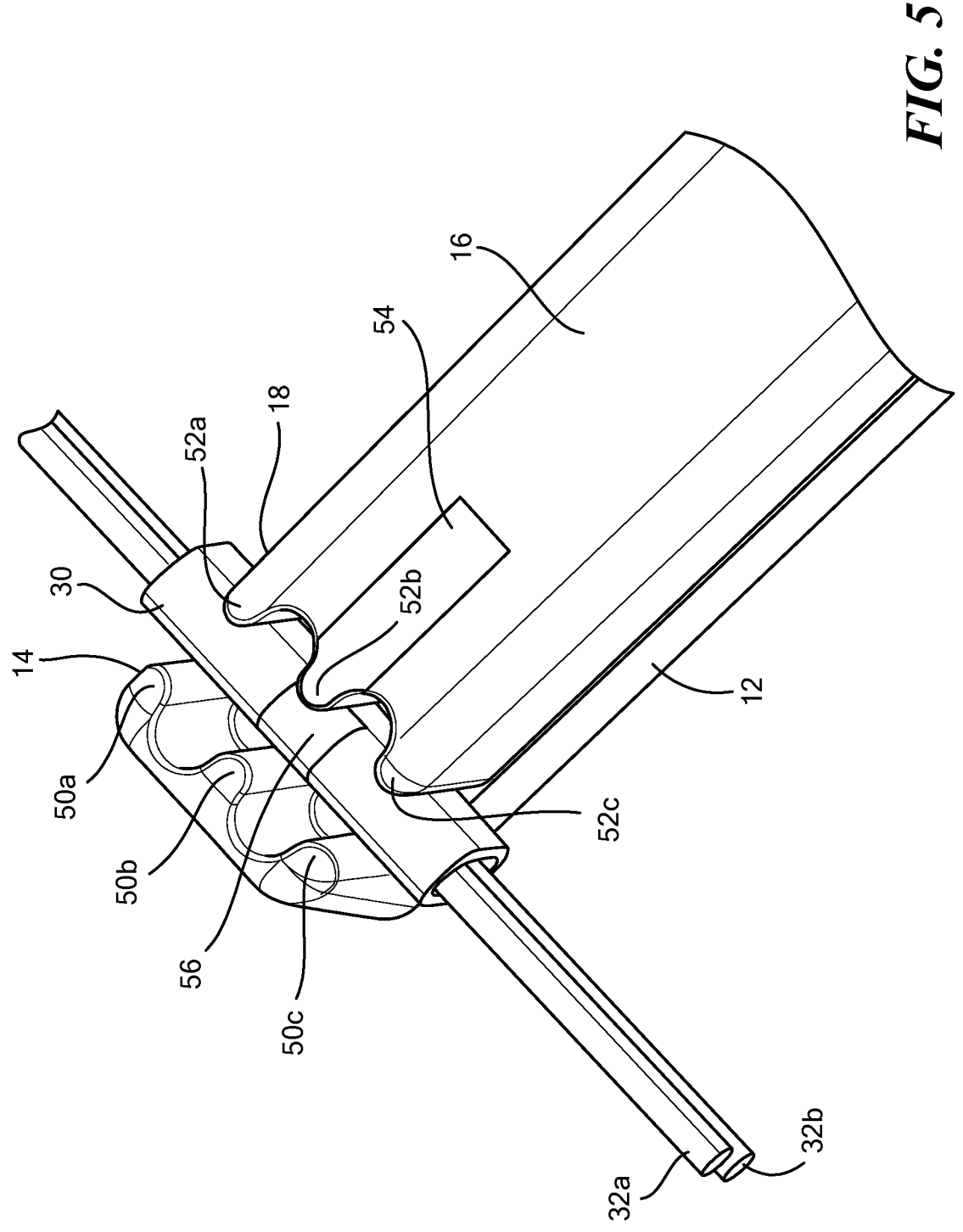
FIG. 5 is a schematic view showing a crimp tube, with two suture ends therein placed between the crimp tool jaws and ready for crimping.

Here, alignment fiducial 54 is associated with crimp member 52b for alignment of a corresponding central alignment fiducial 56 (e.g., 0.06" wide) of crimp tube 30, FIG. 4 in order to guide the user as to the proper central position for the crimp tube in the crimper tool for proper crimping of the crimp tube as shown in FIG. 5. In this example, alignment fiducial 54 extends along crossbar 16 to and then along the face of central crimp member 52b and crimp tube 30 alignment fiducial 56 is centrally located along the extent (length) of crimp tube 30.

As shown in FIG. 4, crimp tube 30 is preferably an 11-gauge regular wall tube preformed into an oval shape and has a preferred wall thickness of approximately 0.020 inches and formed from a biocompatible, ductile material, e.g., 316L stainless steel. The crimp tube is dimensioned so as to allow two legs of suture through without allowing them to cross inside. A 1001b crimp was 0.35" long, between 0.087-0.093" tall, 0.150" wide, and with a wall thickness of between 0.0115-0.0145". A 201b crimp was 0.35" long, between 0.055-0.061" tall, and 0.180" wide. Other dimensions are possible.

Figure 6:
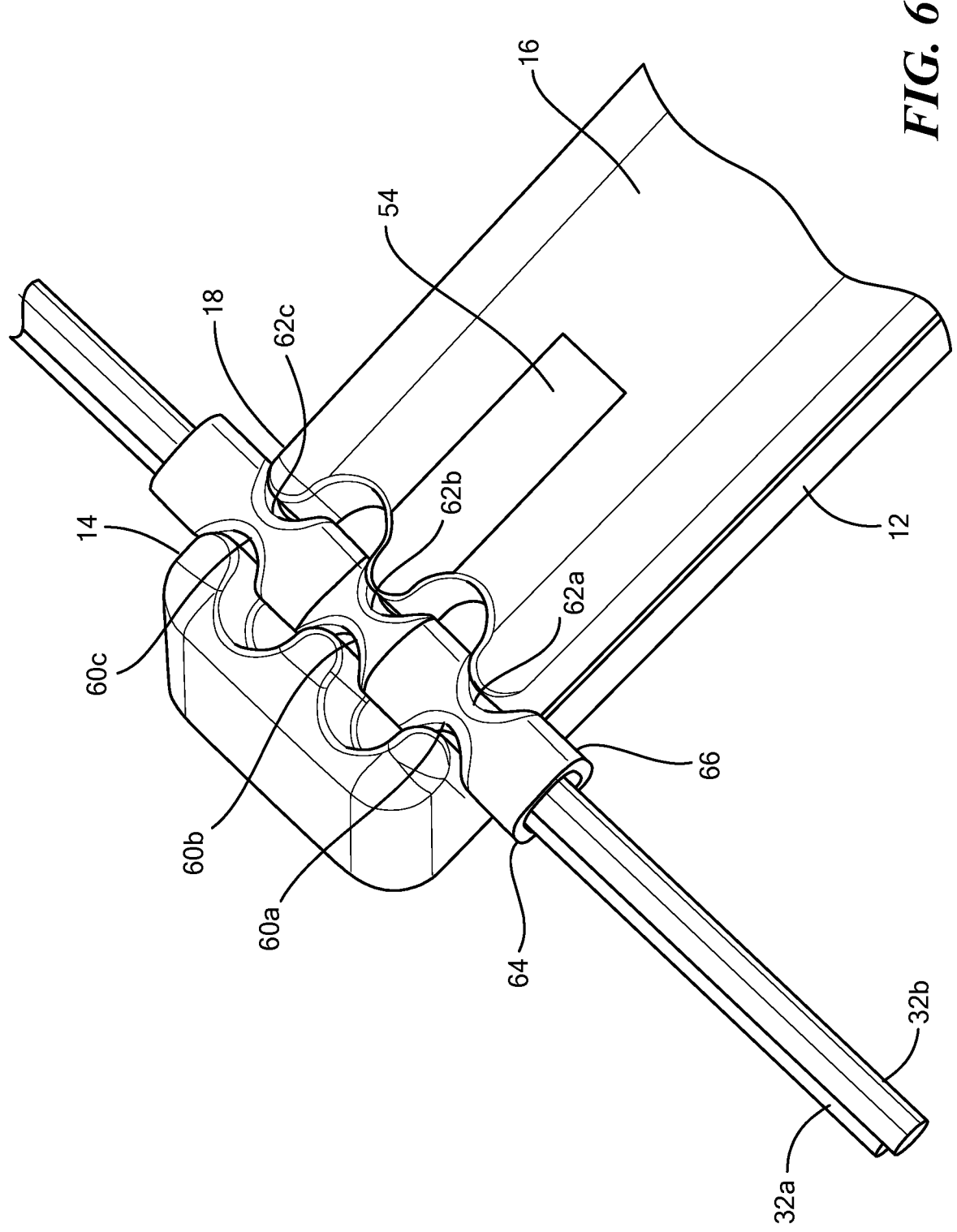
FIG. 6 is a schematic view showing the crimping action of the crimp tool.

This preferred shape for the crimp tube and these preferred dimensions make for easier crimping, easier viewability, and the like as shown in FIG. 6 where the crimp pattern in crimp tube 30 are three spaced crimps with each crimp having opposing deformations across the width of the crimp tube. Three deformations 60a, 60b, and 61b are in the mostly flat top side 64 and three deformations 62a, 62b, and 62c are in the bottom flat side 66 of the crimp tube.

The preferred Ronguer style handle crimp tool allows better visibility than plier type handles and still applies enough force to provide a strong crimping action for the sutures placed in the crimp tube. In the preferred embodiment, the wall thickness of the crimp tube is reduced and the crimp tube is partially pre-crimped into the oval shape shown allowing the modified Ronguer handle to be employed to impart multiple crimps at once in the crimp tube with better visibility and still the holding strength of the crimp tube is adequate and in some cases even better because the pre-crimped tube avoids crossing of the sutures within the tube.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the following claims.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant cannot be expected to describe certain insubstantial substitutes for any claim element amended.

What is claimed is:

1. A medical/veterinary suture crimp tool comprising:

a stationary jaw formed in a distal end of a fixed shank and having across its width and extending at least partially along its length spaced fixed crimp members including at least first, second, and third protruding crimp members;

a moveable jaw formed in a distal end of a linearly driven crossbar and having across its width and extending at least partially along its length, spaced crimp members including at least fourth, fifth, and sixth crimp members opposing, respectively, the first, second, and third protruding crimp members of the stationary jaw;

an alignment fiducial structure associated with said fifth crimp member of the moveable jaw for alignment with an alignment fiducial structure of a crimp tube;

a first handle connected to the fixed shank; and a second handle pivotably connected to the fixed shank and configured to drive the crossbar linearly with respect to the fixed shank to fully crimp the crimp tube causing opposing deformations in the crimp tube via the protruding crimp members of the stationary jaw and the moveable jaw.

2. The crimp tool of claim 1 in which the second handle includes a distal socket about a drive member on the crossbar to linearly drive the crossbar.

3. The crimp tool of claim 1 further including a handle stop limiting the extent of the travel of the crossbar and stopping the moveable jaw from contacting the stationary jaw.

4. A crimp tool comprising:

a stationary jaw formed in a distal end of a fixed shank and having spaced multiple protruding crimp members each configured to provide a deformation on one side of a crimp tube;

a moveable jaw formed in a distal end of a linearly driven crossbar and having spaced multiple protruding crimp members each configured to provide a deformation on an opposite side of the crimp tube thereby creating multiple crimps in the crimp tube when the stationary and moveable jaws are brought together about the crimp tube, each deformation on one side of the crimp tube opposing the deformation on the opposite side of the crimp tube;

an alignment fiducial structure associated with at least one crimp member for alignment with an alignment fiducial structure of a crimp tube;

a first handle connected to the fixed shank;

a second handle pivotably connected to the fixed shank; and means for driving the crossbar linearly with respect to the fixed shank to fully crimp the crimp tube and impart multiple crimps on each side of the crimp tube.

5. The crimp tool of claim 4 in which the means for driving includes a distal socket on the second handle about a drive member on the crossbar to linearly drive the crossbar.

6. The crimp tool of claim 4 further including a handle stop limiting the extent of the travel of the crossbar and stopping the moveable jaw from contacting the stationary jaw.

7. The crimp tool of claim 6 in which the crimp tube has an oval cross-sectional shape.

8. The crimp tool of claim 4 in which the stationary jaw includes at least partially along its length spaced fixed crimp members including at least first, second, and third crimp members, the moveable jaw includes at least across its width and partially along its length at least fourth, fifth, and sixth crimp members opposing, respectively, the first, second, and third crimp members of the stationary jaw.

* * * * *